United States Patent [19]
Hjertén et al.

[11] Patent Number: 5,938,930
[45] Date of Patent: Aug. 17, 1999

[54] METHODS OF IMPROVING PEAK RESOLUTION IN REVERSED-PHASE ELECTROCHROMATOGRAPHY

[75] Inventors: Stellan Hjertén, Uppsala, Sweden; Jia-Li Liao, San Pablo, Calif.

[73] Assignee: Bio-Rad Laboratories, Inc., Hercules, Calif.

[21] Appl. No.: 08/939,367

[22] Filed: Sep. 29, 1997

[51] Int. Cl.⁶ .................................................. B01D 15/08
[52] U.S. Cl. ...................... 210/656; 210/748; 210/198.2; 204/542; 204/545; 204/551
[58] Field of Search ..................................... 210/635, 656, 210/198.2, 502.1, 748, 243; 204/542, 545, 551

[56] References Cited

U.S. PATENT DOCUMENTS

| | | | |
|---|---|---|---|
| 4,315,812 | 2/1982 | Karlson | 204/545 |
| 4,683,042 | 7/1987 | Scott | 204/545 |
| 5,453,382 | 9/1995 | Novotney | 204/545 |
| 5,611,904 | 3/1997 | Cole | 210/656 |
| 5,647,979 | 7/1997 | Liao | 210/198.2 |

*Primary Examiner*—Ernest G. Therkorn
*Attorney, Agent, or Firm*—Townsend and Townsend and Crew LLP

[57] ABSTRACT

Peak resolution in reversed-phase electrochromatography is improved in either of two alternative ways. The first is by a stepwise increase in the concentration of acetonitrile or other equivalent buffer constituent or modifier after the sample has been loaded, and the second is the inclusion of a surfactant in the mobile phase.

6 Claims, 2 Drawing Sheets

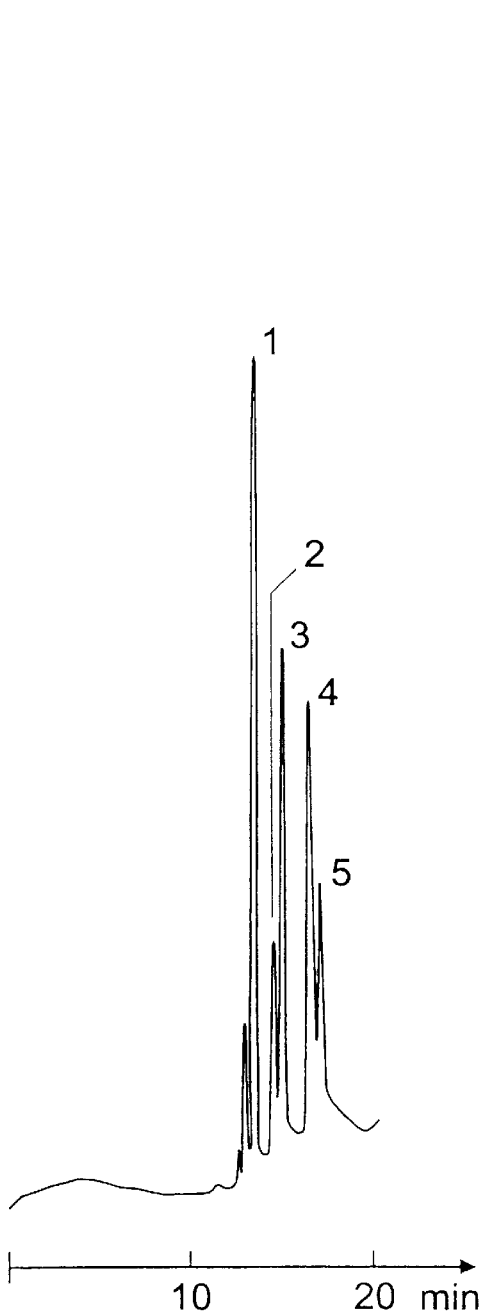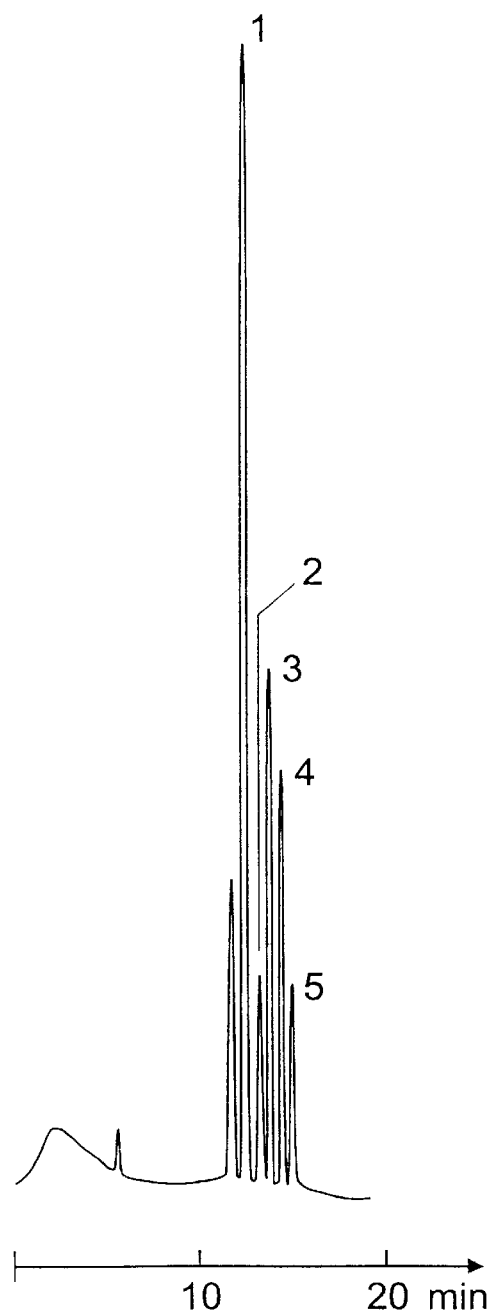
Fig. 1a
Fig. 1b

METHODS OF IMPROVING PEAK RESOLUTION IN REVERSED-PHASE ELECTROCHROMATOGRAPHY This invention relates to reversed-phase electrochromatography.

BACKGROUND AND SUMMARY OF THE INVENTION

Reversed-phase electrochromatography, including reversed-phase ion exchange chromatography and reversed-phase electrophoresis, is a method of choice for the separation and detection of many types of solutes in multi-solute sample mixtures. The term "electrochromatography" is used herein to denote chromatography in wihich electroendosmotic flow is used to drive the mobile phase through a bed of separation media. This is distinct from chromatographic systems in which the mobile phase flow is driven by a pump or other pressure-applying device. Like any chromatography, however, peak resolution in reversed-phase electrochromatography is continually sought to be improved.

The present invention resides in two methods of improving peak resolution in reversed-phase electrochromatography. The first is by the use of a run buffer that contains a desorbing constituent whose concentration is raised after the sample has been loaded, and the second is by the use of a mobile phase containing an ionic or non-ionic surfactant at a concentration below its critical micelle concentration (CMC). The first method has a dual effect—it narrows the sample zone near the entry point of the sample into the separation medium, and it produces a gradient elution due to the gradual equilibration of the mobile phase to the higher concentration. Both effects result in a narrowing of the solute peaks as they emerge from the separation medium and/or are detected. The second method (the use of the surfactant) improves the partitioning of the solutes by increasing the ligand density and/or charge on the stationary phase.

BRIEF DESCRIPTION OF THE FIGURES

FIGS. 1a and 1b are chromatograms of a sample mixture obtained on a continuous bed prepared in accordance with this invention, the separation performed using a running buffer with a constant acetonitrile content (FIG. 1a) and a running buffer with a stepwise increase in the acetonitrile content (FIG. 1b).

DETAILED DESCRIPTION OF THE INVENTION AND PREFERRED EMBODIMENTS

Figure 2A:
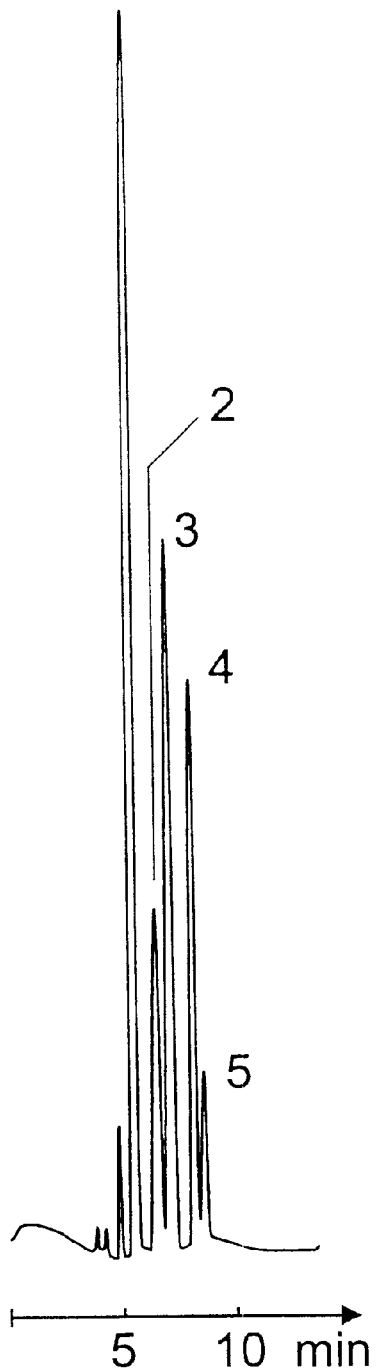
FIGS. 2a and 2b are chromatograms of a sample mixture obtained on a continuous bed prepared in accordance with this invention, using running buffers both with (FIG. 2a) and without (FIG. 2b) sodium dodecyl sulfate.

In accordance with the first aspect of this invention, common buffer constituents or modifiers such as those commonly used to decrease the solute-bed interaction are used. Typical examples are methanol, 2-propanol, acetonitrile and tetrahydrofuran. The effect is achieved by raising the concentration of the constituent or modifier at the rear of the sample zone, i.e., substituting a run buffer with a higher buffer or modifier concentration shortly after the sample has been loaded into the separation medium.

The increase in concentration can vary and is not critical; any increase that will result in an improvement in resolution will suffice. In most cases when the constituent or modifier is a liquid, effective results will be achieved by increasing the concentration of the constituent or modifier by about 10% or more by volume (i.e., adding 10% by volume of concentration, rather than multiplying the concentration by 1.10). In preferred embodiments, the concentration before the increase is from about 35% to about 60%, and the increment of increase is from about 10% to about 30%. Most preferred is a concentration before the increase of from about 40% to about 55% and an increase of from about 15% to about 25%. All percents in this paragraph are volume percents.

The increase is preferably a stepwise increase, immediately after the introduction of the sample.

In accordance with the second aspect of this invention, a mobile phase is used that contains a surfactant at a concentration below the CMC of the surfactant. The surfactant can be anionic, cationic, or nonionic. Typical anionic surfactants are sodium dodecyl sulfate, sodium decyl sulfate, sodium pentanesulfonate, sodium octanesulfonate, and N-lauroyl-N-methyltaurate. The preferred anionic surfactant is sodium dodecyl sulfate. Typical cationic surfactants are cetyltrimethylammonium chloride, cetyltrimethylammonium bromide, tetradecyltrimethylammonium bromide, dodecyltrimethylammonium chloride, dodecyltrimethylammonium bromide, hexyltrimethylammonium bromide, and propyltrimethylammonium bromide. Typical nonionic surfactants are octyl glucoside, polyoxyethylene-23-lauryl ether, polyoxyethylene-20-cetyl ether, polyoxyethylene-2-stearyl ether, and polyoxyethylene-2-oleyl ether.

The CMC's of these surfactants are known to those skilled in the art. The CMC of sodium dodecyl sulfate, for example, is 8.1 mM under specified conditions. For sodium dodecyl sulfate, therefore, preferred concentrations in the mobile phase are within the range of about 0.05 mM to about 7.0 mM, while most preferred concentrations are within the range of about 0.5 mM to about 3.0 mM.

The buffer solutions serving as the mobile phase, including equilibration buffers and run buffers, are otherwise conventional, and may be formulated according to any of the known procedures and compositions known in the chromatography or electrophoresis art. The appropriate buffer for any separation will depend on the desired pH range of the separation, and the selection will be routinely made by those skilled in the art. Typical buffers include citrate, acetate, phosphate, and borate buffers, although biological buffers can also be used where appropriate. A particularly preferred buffer is a phosphate buffer.

The stationary phase in the reversed-phase separations of this invention can be one of any known configuration or chemical composition, including particles, both porous and nonporous, and continuous porous structures. The stationary phase can be retained in a capillary column or a tube of larger diameter than the typical capillary column. Examples of appropriate configurations are found in U.S. Pat. No. 5,647,979, and references (including other patents and patent applications) cited therein, all of which are incorporated herein by reference.

The following examples are offered only for purposes of illustration.

EXAMPLE 1

This example illustrates the first aspect of this invention, i.e., the improvement in peak resolution achieved by increasing the concentration of the run buffer after the sample has been loaded.

A separation medium was prepared by combining the following in 1 mL of 0.015 M Tris-HCl at pH 8.5:

0.12 g piperazine diacrylamide 0.075 g methacrylamide 0.065 g ammonium sulfate

150 μL vinyl sulfonic acid

To 400 μL of this solution were added 50 mg of stearylmethacrylate, melted at 37° C., and 15 μL of TRITON® X-100, a nonionic ethoxylated alkylphenol detergent identified as octylphenoxypolyethoxyethanol having a HLB of 13.5, a product of Union Carbide Corporation, Danbury, Conn., USA. The resulting mixture was heated in a water bath to the cloud point of the detergent and mixed, followed by the addition of ammonium persulfate (5 μL of a 10 weight percent aqueous solution) and 4 μL of N,N,N',N'-tetramethylethylenediamine. The mixture was then immediately drawn into fused silica capillary tubing precoated with γ-methacryloxypropyltrimethoxysilane, the capillary measuring 75 microns internal diameter and having an effective length of 160 mm. Polymerization was allowed to proceed overnight. The capillary was then rinsed with deionized water, acetonitrile, and finally with the mobile phase, which was 4 mM sodium phosphate at pH 7.4, containing 50 volume percent acetonitrile.

A sample consisting of polycyclic aromatic hydrocarbons was prepared by dissolving naphthalene, 2-methyl naphthalene, fluorene, phenanthrene and anthracene, in 4 mM sodium phosphate, pH 7.4, containing 50% (by volume) acetonitrile.

Six minutes after the sample was loaded into the column, a stepwise increase in the acetonitrile concentration to 70 volume percent was made at the rear of the applied sample zone. Two separations were performed—a test run with the stepwise increase in acetonitrile concentration and a control run in which the acetonitrile concentration in the run buffer was maintained constant at 60 volume percent (i.e., no increase after the sample had been loaded).

The chromatogram for the control run is shown in FIG. 1a, where the naphthalene peak is designated by the numeral 1, the 2-methyl naphthalene peak by the numeral 2, the fluorene peak by the numeral 3, the phenanthrene peak by the numeral 4, and the anthracene peak by the numeral 5. The chromatogram for the test run, is shown in FIG. 1b, where the peaks are assigned the same numbers as in FIG. 1a. A comparison of the two chromatograms shows that the combination of zone sharpening and gradient elution in FIG. 1b results in peaks of lesser width and consequently greater resolution compared to FIG. 1a.

EXAMPLE 2

This example illustrates the second aspect of the invention, i.e., the improvement in peak resolution resulting from the inclusion of sodium dodecyl sulfate (SDS) in the mobile phase, at a concentration below its critical micelle concentration.

A column prepared as described in Example 1 was used (except with an effective length of 100 mm rather than 160 mm), with the same sample, the same mobile phase (except for an acetonitrile concentration of 60 volume percent, with no increase), and applied voltage. One separation was performed in this manner, and a parallel separation was performed with the additional inclusion of 1.0 mM SDS in the mobile phase.

Figure 2B:
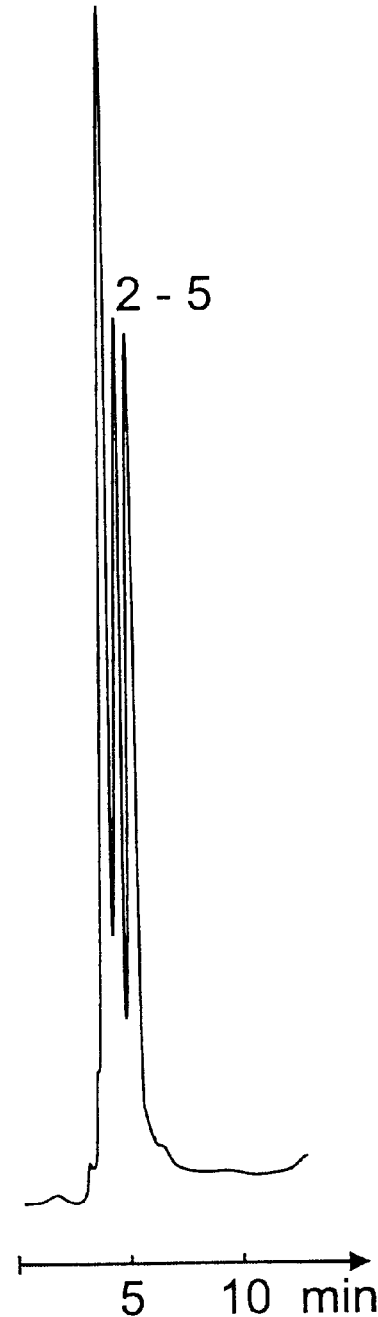

The chromatogram obtained with SDS is shown in FIG. 2a, while the chromatogram obtained without SDS is shown in FIG. 2b. Comparison indicates that the presence of SDS improved resolution so much that a baseline separation was achieved on a column only 100 mm in effective length.

The foregoing is offered primarily for purposes of illustration. It will be readily apparent to those skilled in the art that the materials, proportions, procedural steps and other parameters of the process described herein may be further modified or substituted in various ways without departing from the spirit and scope of the invention.

We claim:

1. A method for detecting individual solutes in a sample comprising a mixture of solutes by reversed-phase electrochromatography, said method comprising:

(a) equilibrating a stationary solid reversed-phase separation medium with an equilibrating buffer containing a species that decreases interaction between said solutes and said separation medium, said species being present in said buffer at a first selected concentration and selected from the group consisting of methanol, 2-propanol, acetonitrile and tetrahydrofuran, and loading said sample into said medium thus equilibrated;

(b) after said sample has been loaded, passing through said separation medium by electrokinetic means a run buffer to effect separation of said solutes into individual solute bands, said run buffer containing said species at a second selected concentration sufficiently greater than said first concentration to produce an increase in resolution among said individual solute bands; and (c) detecting said individual solute bands.

2. A method in accordance with claim 1 in which said species is a liquid additive and said second selected concentration is at least 10% by volume greater than said first selected concentration.

3. A method in accordance with claim 1 in which said species is acetonitrile.

4. A method in accordance with claim 3 in which said first selected concentration is from about 35% to about 60% by volume, and said second selected concentration is from about 10% to about 30% greater than said first selected concentration.

5. A method in accordance with claim 3 in which said first selected concentration is from about 40% to about 55% by volume, and said second selected concentration is from about 15% to about 25% greater than said first selected concentration.

6. A method in accordance with claim 1 in which said reversed-phase separation medium is retained in a capillary.

* * * * *